US007828731B2

United States Patent
Baba et al.

(10) Patent No.: US 7,828,731 B2
(45) Date of Patent: Nov. 9, 2010

(54) ULTRASONOGRAPHIC APPARATUS, ULTRASONOGRAPHIC DATA PROCESSING METHOD, AND ULTRASONOGRAPHIC DATA PROCESSING PROGRAM

(75) Inventors: Hirotaka Baba, Chiba (JP); Yutaka Sato, Chiba (JP); Ryuichi Shinomura, Saitama (JP); Jun Kubota, Chiba (JP)

(73) Assignee: Hitachi Medical Corporation, Tokyo (JP)

( * ) Notice: Subject to any disclaimer, the term of this patent is extended or adjusted under 35 U.S.C. 154(b) by 1561 days.

(21) Appl. No.: 10/488,320

(22) PCT Filed: Sep. 6, 2002

(86) PCT No.: PCT/JP02/09115

§ 371 (c)(1),
(2), (4) Date: Mar. 3, 2004

(87) PCT Pub. No.: WO03/022153

PCT Pub. Date: Mar. 20, 2003

(65) Prior Publication Data

US 2004/0210137 A1 Oct. 21, 2004

(30) Foreign Application Priority Data

Sep. 6, 2001 (JP) ............................. 2001-269682

(51) Int. Cl.
*A61B 8/00* (2006.01)
(52) U.S. Cl. ...................... 600/437; 600/438; 600/440; 600/442; 600/443
(58) Field of Classification Search ................. 600/437, 600/438, 440, 442, 443
See application file for complete search history.

(56) References Cited

U.S. PATENT DOCUMENTS

| 5,456,257 | A | * | 10/1995 | Johnson et al. | 600/458 |
|---|---|---|---|---|---|
| 5,566,674 | A | * | 10/1996 | Weng | 600/443 |
| 5,667,373 | A | * | 9/1997 | Wright et al. | 600/443 |
| 6,117,081 | A | * | 9/2000 | Jago et al. | 600/443 |
| 6,416,477 | B1 | * | 7/2002 | Jago | 600/447 |
| 6,508,770 | B1 | * | 1/2003 | Cai | 600/447 |
| 6,780,152 | B2 | * | 8/2004 | Ustuner et al. | 600/443 |

FOREIGN PATENT DOCUMENTS

| JP | 5-23332 | 2/1993 |
|---|---|---|
| JP | 5-154149 | 6/1993 |
| JP | 11-318892 | 11/1999 |

OTHER PUBLICATIONS

European Office Action dated Nov. 17, 2009. issued in corresponding European Patent Application No. 02 767 918.2.
European Search Report dated Sep. 29, 2009, issued in corresponding European Patent Application No. 02 767 918.2.

* cited by examiner

*Primary Examiner*—Brian Casler
*Assistant Examiner*—James Kish
(74) *Attorney, Agent, or Firm*—Antonelli, Terry, Stout & Kraus, LLP.

(57) ABSTRACT

An ultrasonographic apparatus in which the S/N ratio of a compound image is improved operates by combining a plurality of reception beam signals from probes arranged at different positions relative to a sample, converting the combined ultrasonic beam into a luminance signal, and displaying the luminance signal.

21 Claims, 7 Drawing Sheets

ULTRASONIC IMAGE

Fig. 5b

ULTRASONIC IMAGE

Fig. 5c

ULTRASONIC IMAGE

Fig. 5d

COMPOUND IMAGE

Fig. 6a

ULTRASONIC IMAGE

Fig. 6b

COMPOUND IMAGE

Fig. 7a

ULTRASONIC IMAGE

Fig. 7b

COMPOUND IMAGE

ULTRASONIC IMAGE

Fig. 10b

COMPOUND IMAGE

ULTRASONOGRAPHIC APPARATUS, ULTRASONOGRAPHIC DATA PROCESSING METHOD, AND ULTRASONOGRAPHIC DATA PROCESSING PROGRAM

TECHNICAL FIELD

The present invention relates to an ultrasonic imaging apparatus of the type used, for example, in medical diagnosis, an imaging data processing method, and an imaging data processing program, and more particularly, the invention relates to a technique for obtaining a cross-sectional image of high image quality, generally referred to as a compound scan image, in which image signals acquired by scanning in various directions are synthesized and displayed as a single image.

BACKGROUND OF THE INVENTION

An ultrasonic imaging apparatus is designed to transmit ultrasonic waves to an object to be examined through an ultrasound probe that is applied to a body surface of the object, and to receive reflected waves (echo signals) from inside of the object. In this way, it is possible to display cross-sectional images of portions of the object on the basis of the echo signals for use in medical diagnosis and the like.

Generally, an ultrasound probe is formed by arranging a plurality of transducers at even intervals in a straight line, a curved line, or a plane. For example, in an ultrasonic imaging apparatus of the linear scan type, an aperture is formed by selecting a transducer group in which the transducers are to be driven at the same time by an aperture selecting switch, and this aperture is sequentially moved so as to scan the ultrasonic beams inside an organism or an inorganic object. Scanning is performed in the same manner as that used in an ultrasonic imaging apparatus of the convex scan type.

In both the apparatuses of the linear scan type and of the convex scan type, when a direction or an angle of the ultrasonic beam is predetermined, a plurality of received beam signals acquired by the scan are stored in memory cells at addresses set in correspondence with each beam direction or angle, and an image is displayed.

On the other hand, in an ultrasonic imaging apparatus of the compound scan type, as disclosed in Japanese Unexamined Patent Publication No. JP-A-64-62133 and JP-A-5-285146, a probe is moved along the surface of the object, and an image is obtained from a received beam signal corresponding to an ultrasonic beam signal at various angles and at various positions, and these images are combined in real time. In this case, because the positions and the angles of the ultrasonic beams vary, the position and the angle of the received beam signal are calculated by detecting positional information of the probe in real time, and then images are synthesized on the basis of this information. Accordingly, by superposing the same cross-sectional images, a boundary between mediums in parallel with an ultrasonic beam and inside of an object to be examined, which boundary is only insufficiently depicted through a cross-sectional image in a single direction, can be clearly depicted. Further, a dark portion appears due to a small luminance signal caused by multiple reflection or behind a strong reflection body. There is an effect that the image of such a portion is improved by superposing images taken from various directions.

However, according to the above-described conventional method of compound image generation, image synthesis is performed after converting the received beam signals into luminance signals. Therefore, the method does not demonstrate an effect of improving the signal to noise ratio (S/N ratio) in the known opening synthesis by superposing received beam signals having phase information and obtaining the resulting interference.

Besides, since an ultrasonic image can be obtained only within an effective FOV (field of view) of the probe, for example, the image of a portion of an object to be examined having a size larger than the effective FOV can be obtained through a plurality of ultrasonic images which are obtained by moving the probe in a longitudinal direction and joining these images. The obtained image is referred to as a panoramic image, and such a technique is disclosed in Japanese Unexamined Patent Publication No. JP-A-2001-104312.

In the above-described method of panoramic image generation, the angle and position of the probe are detected and the ultrasonic images are joined to make a panorama image. However, since the panoramic image synthesis based on detection of the angle and position of the probe deals with luminance signals, signal processing in consideration of phase signal components of echo signals is not considered in the processing the signals.

An object of the present invention is to improve the S/N ratio of a compound image in an ultrasonic imaging apparatus.

SUMMARY OF THE INVENTION

To achieve the above-stated object, an ultrasonic imaging apparatus according to the present invention includes: means for combining a plurality of received beam signals having a respectively different positional relation relative to an object to be examined, these signals being obtained from an ultrasound probe; means for converting the synthesized received beams into luminance signals; and means for displaying the thus-converted luminance signals.

That is, because the plurality of received beam signals are combined before conversion into luminance signals, phase information of the received beam signals is not lost, whereby the S/N ratio can be improved by combining the received beam signals in such a way as to make them interfere with each other.

Further, the combining means includes means for acquiring a first received beam signal from the ultrasound probe in a first positional relation to the object; and means for acquiring a second received beam signal from the ultrasound probe in a second positional relation, which is different from the first positional relation, wherein the first received beam and the second received beam are combined.

Further, the ultrasonic imaging apparatus includes position detecting means for detecting the first positional relation and the second positional relation; and compound signal constructing means for combining the first received beam and the second received beam on the basis of the positional relations detected by the position detecting means.

In this case, the compound signal constructing means includes a memory having memory cells, the addresses of which are arranged in correspondence with a scanning plane of the ultrasonic beams. By stacking and memorizing the received beam signal output by digital phase adding means at corresponding memory cell addresses, the signal can be combined with another received beam signal. Further, at the time of the synthesis, the view angle of the joint cross-sectional image can be easily enlarged by adjusting the memory addresses at a certain ratio.

Further, the position detecting means may find the position and the direction of the ultrasound probe based on the interrelation between a plurality of sequential images. According to this method, it is possible to avoid complication of the scanning on the object, while detecting the position and direction of the probe attached to a mechanical position detecting device. Meanwhile, according to the present invention, a mechanical position detecting device may be employed, or a magnetic sensor may be used. Moreover, a position sensor may be built in the probe.

Further, it is desirable to provide sound speed distribution measuring means for finding a sound speed distribution in a medium on an ultrasonic scanning plane on the basis of the interrelation among the echo signals forming the received beam signals of the respective transducers and to correct the positional relations between the received beam signals and the object on the basis of the found sound speed distribution in the compound signal constructing means. According to this, it is possible to correct an error of the positional relation among the received beam signals generated due to distortion in path distance and the time of the beams due to the difference in the sound velocities of the various mediums in the object. Accordingly, the compound signals can be precisely synthesized, and the preferred image contrast can be clearly created.

Further, signal alternating means for alternating the polarity of a received beam signal is provided. The compound signal constructing means may be designed to respectively generate a signal obtained by combining the received beam signal and a signal obtained by combining reverse received beam signals output by the signal alternating means, respectively, and it may add up the generated synthesized received beam signals. In other words, a higher harmonic cross-sectional image having a high image quality can be obtained by synthesizing a received beam signal of the regular phase and that of the reverse phase. Particularly, because higher harmonic cross-sectional images can be obtained by using an identical received beam signal, the number of picture images obtained per unit time (frame rate) is not deteriorated in comparison with the cases where two ultrasonic beams, of the regular phase and of the reverse phase, are separately scanned so as to obtain a higher harmonic cross-sectional image, as obtained in the conventional technique.

Further, by controlling the direction of the ultrasonic beams in accordance with the position and direction of the ultrasound probe with respect to the object found by the position detecting means, a transmitted wave focusing function may be added to the apparatus. Accordingly, a cross-sectional image acquired from a direction different from that of a standard cross-sectional image is superposed so as to create an accurate cross-sectional image.

Further, sound speed layer structure measuring means is provided for measuring the structure of a sound speed layer in a medium on the ultrasonic wave scanning plane on the basis of the interrelation among the echo signals of the respective transducers, forming the received beam signals. It is desirable that the compound signal constructing means corrects for distortion in the path distance and the time of the received beam signals on the basis of the sound speed layer structure.

BEST MODE FOR CARRYING OUT THE INVENTION

Hereinafter, various embodiments of the present invention will be described with reference to the accompanying drawings.

First Embodiment

Figure 1:
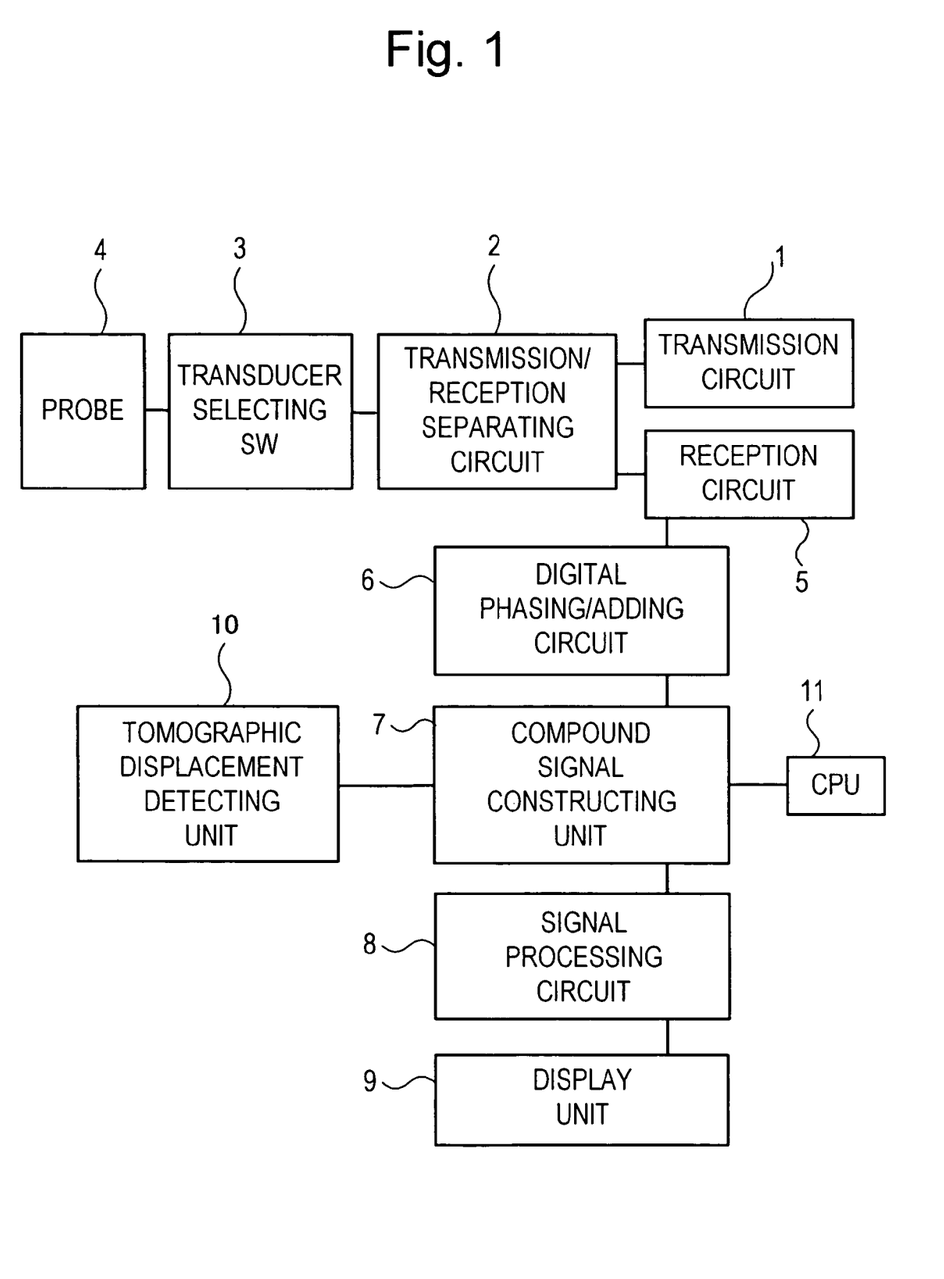
FIG. 1 is a block diagram showing one embodiment of an ultrasonic imaging apparatus according to the present invention.

FIG. 1 is a block diagram showing one embodiment of an ultrasonic imaging apparatus. In this figure, an ultrasonic pulse signal for driving a probe 4 is supplied from a transmission circuit 1 via a transmission/reception separating circuit 2 and a transducer selecting switch (SW) 3. The probe 4 has a plurality of transducers. The transducer selecting switch 3 is formed by a multiplexer circuit, which is designed to select and thus switch a plurality of transducer groups (aperture) to be driven at the same time. The transmission circuit 1 is designed to generate an ultrasonic pulse signal for driving the transducer, and to apply a delay to the ultrasonic pulse signals to be supplied to a plurality of the transducers forming the aperture, so as to control the direction and the focal point of the ultrasonic beams transmitted to the inside of the object.

Reflected signals (echo signals) of the ultrasonic beams generated from the object are received by each transducer and converted into electrical signals.

The echo signals that are converted into electrical signals are routed from the transmission/reception separating circuit 2 to a reception circuit 5 via the transducer selecting SW 3. That is, the transmission/reception separating circuit 2 passes a signal from the transmission circuit 1 to the transducer when an ultrasonic wave is transmitted, and it passes a signal from the transducer to a reception circuit 5 when receiving a signal.

The reception circuit 5 amplifies weak echo signals, converts them into digital signals, and outputs them to a digital phasing/adding circuit 6. The digital phasing/adding circuit 6 makes uniform the phases of the digital echo signals output by the reception circuit 5, adds up the phased signals to form a received beam signal, and outputs it to a compound signal constructing unit 7. The compound signal constructing unit 7 combines the received beam signals and other received beam signals previously measured, and adjusts for the respective positional relation to the object, so as to generate a compound signal. A signal processing circuit 8 performs processes for creating an image of the compound signal output by the compound signal constructing unit 7. That is, it performs detection, logarithmic compression, and y-correction on the compound signal, and, thus, it generates an image signal in the form of a luminance signal. The image signal generated by the signal processing circuit 8 is routed to a display unit 9, where the ultrasonic beam scan is converted into an image display scan, whereby an image is displayed on a display monitor.

A cross-sectional image displacement detecting unit 10 detects an amount of relative displacement between the object and the probe 4, and it detects phenomenon generally referred to as body movement, such as beats inside the object, such as heart beats in a human body, as a displacement amount, and outputs signals representing them to the compound signal constructing unit 7. In the cross-sectional image displacement detecting unit 10, for example, a system which detects displacement of a probe from correlation between images sequentially obtained may be employed. A system utilizing a probe position detecting arm and a magnetic sensor also may be used. The point is, any conventional method may be applied as long as it can detect the positional relationship between the wave probe 4 and the object. A CPU (central processing unit) 11 operates to integrate and control the above-described constituent elements.

Operations of the thus-constructed ultrasonic imaging apparatus will be described next. First, an operator gives instructions for initiating the functions of the ultrasonic imaging apparatus. For example, before beginning examination, the apparatus is instructed that a compound image is to be obtained. In this case, the operator can select from among creating a compound image from an ultrasonic beam signal, combining images using a luminance signal, performing compound image creation with the field angle enlarged, and combining images without enlarging the field angle. For this purpose, an image combining mode switching device may be provided in the console so as to effect creation of a compound image with a selected mode.

After selecting the functions of the ultrasonic imaging apparatus in the above-described manner, the operator applies the probe 4 to a body surface in a region of the object to be examined, and inputs instructions to begin an ultrasonic scan from the console. In response thereto, the aperture selection, transmission delay data, and reception delay data are set to the transducer selecting switch 3, transmission circuit 1, and reception circuit 5, respectively. Then, in response to the instruction for selecting the compound image creation mode, the compound image signal constructing unit 7 is selected and a scan of the ultrasonic beams is begun. Driving pulses respectively provided with a time delay are input from the transmission circuit 1 to the transducer selecting switch 3 via the transmission/reception separating circuit 2 corresponding to each transducer forming the aperture on the probe 4. The transducer selecting switch 3 switches connection of the driving pulses so that they are output to each corresponding transducer, whereby a selected transducer group is driven by the driving pulse output by the transducer selecting switch 3.

The transducers of the selected transducer group are driven in order from the less-delayed signals to transmit the ultrasonic waves. The delay time of the ultrasonic waves transmitted to the inside of the living body is adjusted by the transmission circuit 1 so that the wave surfaces of the ultrasonic waves arrive at a predetermined focal point of the transmitted wave with the same phase at the same time. If a wave passes through tissues having different acoustic impedances inside the living body in the process of propagation, a part of the ultrasonic beams is reflected at that interface and echoes return toward the probe. The echoes sequentially return toward the probe in the order of the depth inside the living body through which they propagate. These echoes are received by the transducers which have been driven for transmission, or transducer groups having larger apertures with the passage of time are selected and switched over, and the received echoes are converted into electrical echo signals.

The echo signals which are converted into electrical signals by the transducer are input into the reception circuit 5 via the transducer selecting switch 3 and the transmission/reception separating circuit 2, where the echo signals are separately amplified at each element line (channel) of the transducers and are converted into digital signals at each channel. The thus-digitalized echo signals are input into the digital phasing/adding circuit 6. In the digital phasing/adding unit 6, the digitalized echo signals, which have been provided with a time delay corresponding to the respective ultrasonic transducers, are delayed at each channel and added up. That is, the echo signals are added and their time phases are made uniform so that the echoes reflected at a certain point (each point on the received beams) in the object seem to appear at each channel at the same time, whereby any noise included in the echoes is reduced. Further, by performing filtering, signals in a necessary signal band are extracted to acquire a received beam signal. Those processes in the reception circuit 5 are known as a dynamic focus method.

The received beam signal generated by the reception circuit 5 is input into the compound signal constructing unit 7, where compound processing according to the present invention is carried out. That is, received beam signals having phase information, yet to be converted into luminance signals, are combined, and they are made to interfere with each other, whereby the S/N ratio can be improved. Accordingly, the compound signal constructing unit 7 is designed to be able to deal with a complex signal and to operate rapidly, which is different from a conventional apparatus. Here, the purpose of creating a compound image is, as described above, to clearly image the interface between mediums parallel to an ultrasonic beam in the object, and to reduce dark portions appearing behind a body producing multiple reflections or a strongly reflecting body by superposing images obtained from various directions. Accordingly, when one cross-sectional image is obtained, another image of this cross-sectional image is taken with ultrasonic beams at a different position or in a different direction, and these two images are combined. In this synthesis, because received beam signals obtained from the same portion of the object have to be combined, it is necessary in creating a compound image to measure the direction of the received beams, the relation between the received beams and the depth, and the positional relation between those and the object, and to make adjustments for the positional relation between the received beams for two images.

The compound signal constructing unit 7 according to this embodiment has two RAMs constituted of memory cells, the addresses of which are two-dimensionally arranged in correspondence with the scanning plane of the ultrasonic beams. One is a received beam signal RAM for storing a received beam signal input in one measurement, and the other is a compound signal RAM for storing a received beam signal measured in a preceding measurement or a compound signal already created. The addresses of these RAMs are set corresponding to a two-dimensional scanning plane based on the center of the probe in each measurement and the direction of the probe (vertical direction).

Here, the central position and the direction of the probe are detected by the cross-sectional image displacement detecting unit 10. The cross-sectional image displacement detecting unit 10 employs a conventional method of finding a position and a direction of the ultrasound probe relative to the object from the correlation between a plurality of images sequentially obtained, for example. It is thus possible to avoid the complication of performing a scan on the object while detecting the position and the direction of the probe attached to a mechanical position detecting device. However, the present invention is not limited thereto, and a mechanical position detecting device also may be employed. Further, a known magnetic sensor also may be used.

By setting the measurement standard as the thus-detected central position and direction of the probe, and, on the basis of an estimated value of the speed of sound in the medium and information of the time length between ultrasonic transmission and reception, the relation between a received beam signal and its depth is determined from the path distance of the ultrasonic waves, and the signals of the respective portions corresponding to received beam signals in the depth direction are stored in memory cells at the corresponding addresses of the received beam signal RAM.

Meanwhile, in the same manner as in the above-described received beam signal RAM, the compound signal RAM stores compound signals created in the preceding measurement (in an initial state, received beam signals). Accordingly, by reading out the signals corresponding to the same portion from both RAMs and performing a calculation, the received beam signal and the compound signal can be combined. However, it is necessary to coordinate the position of the addresses of the compound signal RAM and that of the received beam signal RAM, because the position and the direction of the probe are different. Next, the compound processing will be described in detail.

For example, on the basis of the compound signal RAM, a search is made for the address of a memory cell of the received beam signal RAM, in which the received beam signal is superposed and recorded on the memory cell. If a portion corresponding to the received beam signal is not stored in the memory cell corresponding to the retrieved address, the correct address is found by appropriate interpolation using a known method. Then, the portion corresponding to the received beam signal is stacked and recorded on the memory cell of the compound signal RAM. By executing this processing for all memory cells of the compound signal RAM, the received beams obtained in two measurements can be combined on the memory. The compound signals in the compound signal RAM are output to the signal processing circuit 8. In the signal processing circuit 8, detection, logarithmic compression, and y-correction are performed on the compound signals so as to generate an image signal in the form of a luminance signal. The image signal is displayed on the display monitor via the display unit 9.

A formula which may be used for finding an address of a memory cell of the received beam signal RAM for creating the above-described compound signal is, for example:

$$Xb=\{(Xc-X)\cos\theta+(Yc-Y)\sin\theta\}/\alpha\ Yb=\{(Yc-Y)\cos\theta+(Xc-X)\sin\theta\}/\beta$$

wherein

X: a probe position on a coordinate axis in a horizontal direction in relation to an initial image;

Y: a probe position on a coordinate axis in a vertical direction in relation to an initial image;

θ: a beam direction in relation to the direction downward from the initial image;

Xb: an address of the received beam signal RAM (scanning direction of the received beam);

Yb: an address of the received beam signal RAM (direction of the received beams);

Xc: an address of the compound signal RAM (horizontal direction of a display monitor);

Yc: an address of the compound signal RAM (vertical direction of a display monitor);

α: an amplification coefficient between the received beam signal RAM and the compound signal RAM (scanning direction of the received beams); and β: an amplification coefficient between the received beam signal RAM and the compound signal RAM (direction of the received beams).

In the above formula, the initial image is the cross-sectional image which is first constructed after an operator instructs the system to begin synthesis of a compound image, or it is an image immediately preceding a currently noticed cross-sectional image even when initiation of synthesis of the compound image is not instructed. The cross-sectional images input after the initial image are rotated and moved with regard to coordinate axes of the initial image, and they are combined and output as a compound image.

In this manner, ultrasonic transmission and reception and signal processing therefor are repeatedly performed, while selecting and switching the transducers or changing the direction of ultrasonic beams, and an image is produced by received beam signals input at each repetition of transmission and reception. The stored contents in the memory, which have been made into an image, are read out in sync with the scan of a CRT display device or the like, and the inside of a living body is thus imaged by the ultrasonic scan. This imaging is repeatedly performed a plurality of times, and the thus-obtained images are sequentially processed by the compound signal constructing unit 7 and are displayed as a compound image.

Figures 5A, 5B:
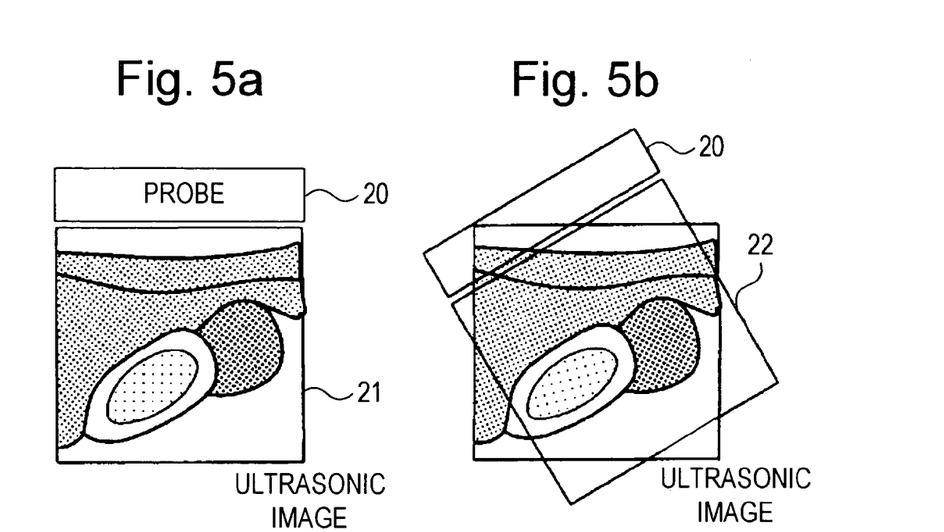
FIGS. 5a to 5d are diagrams showing one mode of a compound scan performed by a linear-type scanning probe.
Figures 5C, 5D:
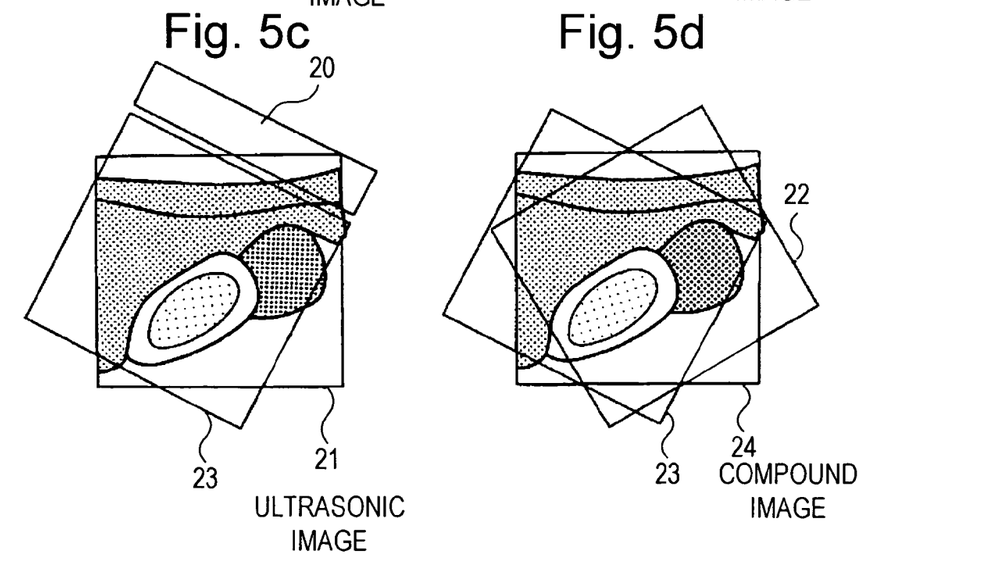
Figures 6A, 6B:
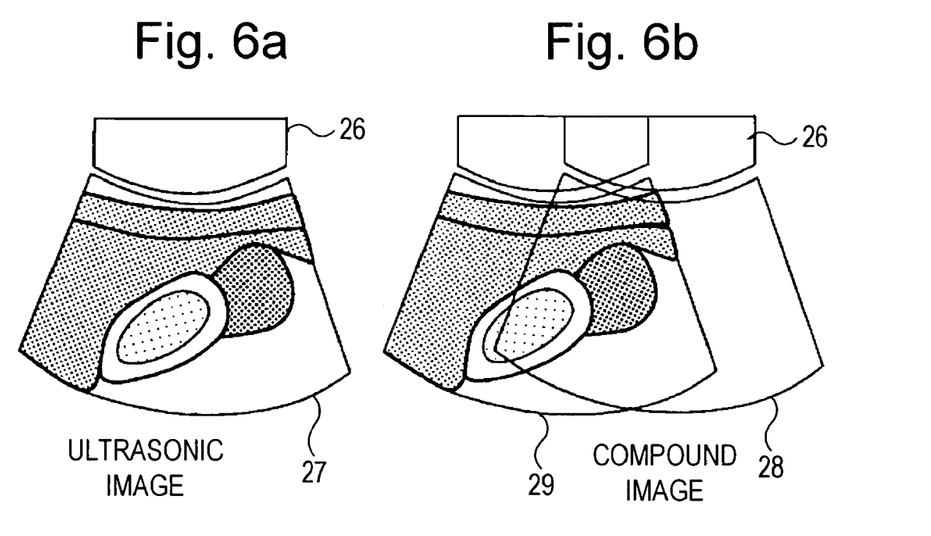
FIGS. 6a and 6b are diagrams showing one mode of a compound scan performed by a convex-type scanning probe.

FIG. 5(a) to 5(d) show one example of the compound image synthesis of the linear scan type. In the figures, a probe 20 is schematically illustrated so as to show the positional relation thereof to an ultrasonic image. FIG. 5(a) shows an initial image 21, FIG. 5(b) shows an ultrasonic image 22 obtained in the subsequent ultrasonic imaging, FIG. 5(c) shows an ultrasonic image 23 obtained in the further subsequent ultrasonic imaging, and FIG. 5(d) shows a compound image 24 created by combining these images. In an apparatus of the convex scan type, as shown in FIG. 6(a) and 6(b), after an image 27 is obtained by a probe 26 of the convex type, the position of the probe 26 is moved to obtain an ultrasonic image 28, and a compound image 29 is created by combining these images.

A method of performing compound synthesis on a RAM, as provided in this embodiment, is conventionally known in ultrasonic imaging utilizing a luminance signal. However, this embodiment is characteristic in that the compound synthesis is performed using a complex signal after phasing and addition before conversion into a luminance signal. Accordingly, because phase information of received beam signals is not lost, the S/N ratio can be improved by combining the signals and thus making them interfere with each other.

Second Embodiment

Generally, there is a known problem in performing the compound operation in that the image quality is deteriorated when a plurality of received beam signals cannot be superposed correctly in regard to positional relation because of certain errors. For example, if errors increase so as to accumulate slight errors in beam position information, the accuracy of a superposed position is deteriorated. One of the factors causing errors to occur in beam position information is that an object to be examined is formed by mediums having various sound speeds. That is, if there are mediums having various sound speeds, the speed of an ultrasonic beam passing through the plurality of mediums is increased or decreased thereby, and, as a result, the cross-sectional image might be distorted. Particularly, each of the cross-sectional images measured from different angles and positions by the probe has a different degree of distortion. In a method of performing the compound synthesis by storing phase information, as in the first embodiment, when a compound signal is constructed from received beam signals which are obtained from two directions and are differently distorted, the image quality is extremely deteriorated in comparison with a conventional method which superposes luminance signals, and the compound image becomes blurred. Therefore, it is effective to correct the positional information of received beam signals to be superposed in correspondence with the variation of the sound speeds in the medium.

Figure 2:
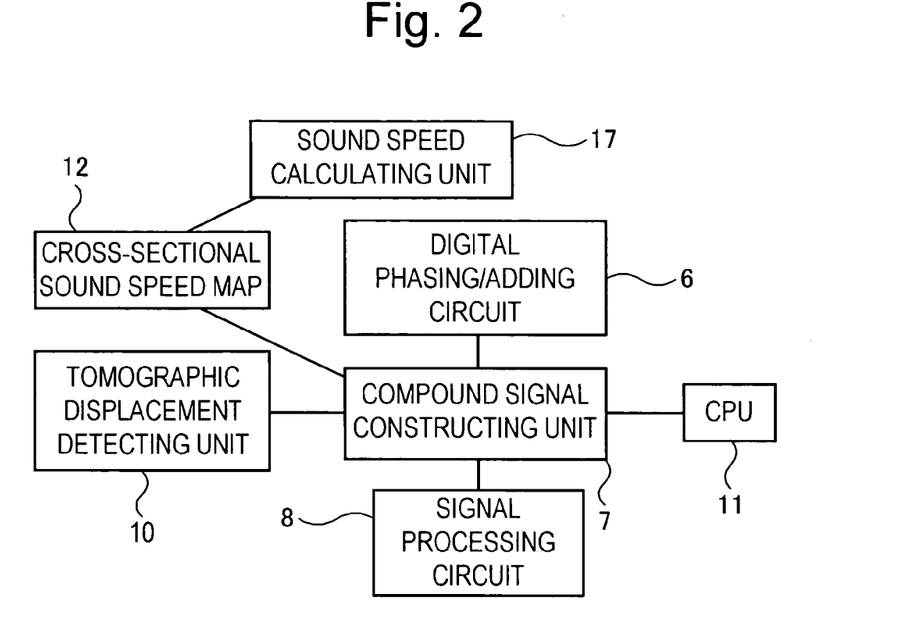
FIG. 2 is a block diagram showing another embodiment of an ultrasonic imaging apparatus according to the present invention.

FIG. 2 is a block diagram showing a main part of an ultrasonic imaging apparatus according to an embodiment of the present invention, where the positional information of received beam signals is corrected according to the speed of sound in the medium. As shown in this figure, in addition to the First embodiment, an ultrasonic imaging apparatus according to this embodiment is provided with a sound speed calculating unit 17 for calculating the speed of sound in each portion in a cross-sectional image and a cross-sectional sound speed map 12 for storing the calculated sound speed. There is also a compound signal constructing unit 7 for correcting for positional information of the received beam signals on the basis of sound speed distribution data from the cross-sectional sound speed map 12 and for performing compound synthesis. The echo signals of each channel, before being added together and formed into a beam signal by the digital phasing/adding circuit 6, are input into the sound speed calculating unit 17, where the phase difference between the respective channels is found by calculating a mutual correlation between those channel signals. The phase difference is not detected as long as the speed of sound in a medium estimated in advance coincides with the actual speed of sound in the medium. However, since the estimated speed of sound is generally different from the actual speed of sound in the medium, a phase difference is detected. For example, when values of the phase difference for each channel are arranged on a graph, they all fall into a straight line in the graph indicating a phase difference of zero at all channels if the phase difference cannot be detected. Also, if the estimated speed of sound is different from the actual speed of sound, the values of the phase difference at the respective channels make a straight line having an inclination. It has been already found that the inclination becomes steeper as the difference between the estimated speed of sound and the actual speed of sound becomes larger. By using the above-described relation, it is possible to simulate the gap between the estimated speed of sound and the actual speed of sound in the medium and, thus, to derive in advance the relation between the inclination of the straight line made by a phase difference at each channel and sound speeds in the mediums. And, by creating a chart of this relation between the sound speeds in the mediums and the inclination of the phase difference distribution and storing this information in an internal memory, the speed sound in a medium can be easily found. That is, the phase differences between each channel are calculated, the inclination of the phase difference distribution of all channels is calculated using a method of least square error or the like, and the above-created comparison chart of the relation between the inclination and the sound speeds is referred to, whereby an average speed of sound in mediums included in the path to the focal point can be found. By storing the value of the speed of sound measured at each focal point in this manner in an address corresponding to each focal point in a memory unit of the cross-sectional sound speed map 12, a sound speed map can be easily created.

When the compound signal constructing unit 7 calculates a value of a received beam signal input from the digital phasing/adding circuit 6, the value is stored superposed in the compound signal RAM, the speed of sound in a medium in the object is read out from the cross-sectional sound speed map 12, and the address of the received beam signal RAM is corrected in accordance with the speed of sound in the medium. Then, components of the received beam signal stored at the corrected address and the value stored in the compound signal storing RAM are superposed and a calculation is performed, and the result is written in the compound signal RAM.

At this time, a formula for finding the address of a memory cell of the received beam signal to create a compound signal is, for example, indicated below. Incidentally, a value in the sound speed map 12 is an average sound speed value at between a portion near the probe and a deeper region, and the addresses are constructed to have an identical interval of data in both the received beam signal RAM scanning direction and the received beam direction (sampling intervals between adjoining addresses are made identical in the RAMs in those directions). Further, because the distortion mentioned above is generated by mediums having different sound speeds in the received beam direction, correction of addresses of the received beam signal RAM is performed and it is hypothesized that the ultrasonic beams are aligned at an interval of beam scanning determined by the pitch between the arranged transducers in the beam scanning direction.

$$Xv=\{(Xc-X)\cos\theta+(Yc-Y)\sin\theta\}/\alpha\ Yv=\{(Yc-Y)\cos\theta+(Xc-X)\sin\theta\}/\beta\ Xb=XvYb=Yv\times V/\gamma(Xv,Yv)$$

X: a position of the probe on a coordinate axis in a horizontal direction in relation to an initial image Y: a position of the probe on a coordinate axis in a vertical direction in relation to the initial image θ: a beam direction in relation to the direction downward from the initial image Xb: an address of the received beam signal RAM (direction of received beam scanning)

Yb: an address of the received beam signal RAM (direction of a received beam)

Xc: an address of the compound signal RAM (horizontal direction of the display monitor)

Yc: an address of the compound signal RAM (vertical direction of the display monitor)

Xv: an address of the sound speed map RAM (direction of received beam scanning)

Yv: an address of the sound speed map RAM (direction of the received beam)

α: an amplification coefficient between the beam signal RAM and the sound speed map RAM (direction of received beam scanning)

β: an amplification coefficient between the beam signal RAM and the sound speed map RAM (direction of a received beam)

γ(Xv,Yv): a value of the sound speed map RAM (value of an address Xv, Yv)

V: a standard sound speed in the medium (1530 m/s according to JIS for medical ultrasound cross-sectional image apparatus)

Third Embodiment

Generally, it is known that when an ultrasonic wave passes through the inside of an object to be examined, its waveform is distorted due to the physical nature of the medium, whereby the degree of distortion gradually becomes larger as the path length becomes longer, and the ratio of higher harmonic wave components to fundamental wave components increases. Also, it is known that among the higher harmonic components, the second harmonic wave is particularly extracted and is made visible. In a known method therefor, for example, a transducer is driven by a normal-phase waveform to transmit ultrasonic waves to the inside of the object, reflected ultrasonic wave signals are received, and these signals are added and phased so as to be formed into a received beam signal having phase information to be stored. Next, the phase of the waveform transmitted is inverted, ultrasonic waves are similarly transmitted and received, and these waves are phased and added so as to generate a received beam signal having phase information. Then, a sum of this signal and the above-described received beam signal of the normal-phase waveform is calculated so as to make the signal visible. By doing so, the fundamental wave can be substantially removed from the signal transmitted and received first, and the size of the second higher harmonic wave is substantially doubled. Accordingly, this is a very effective method of second harmonic visualization. However, in carrying out this method, it is always necessary to perform transmission and reception two times for obtaining one second harmonic image, whereby the number of images per time unit (frame rate) is cut in half in comparison with the normal case. Therefore, a method of visualizing second harmonic waves without reducing the frame rate is desired.

Figure 3:
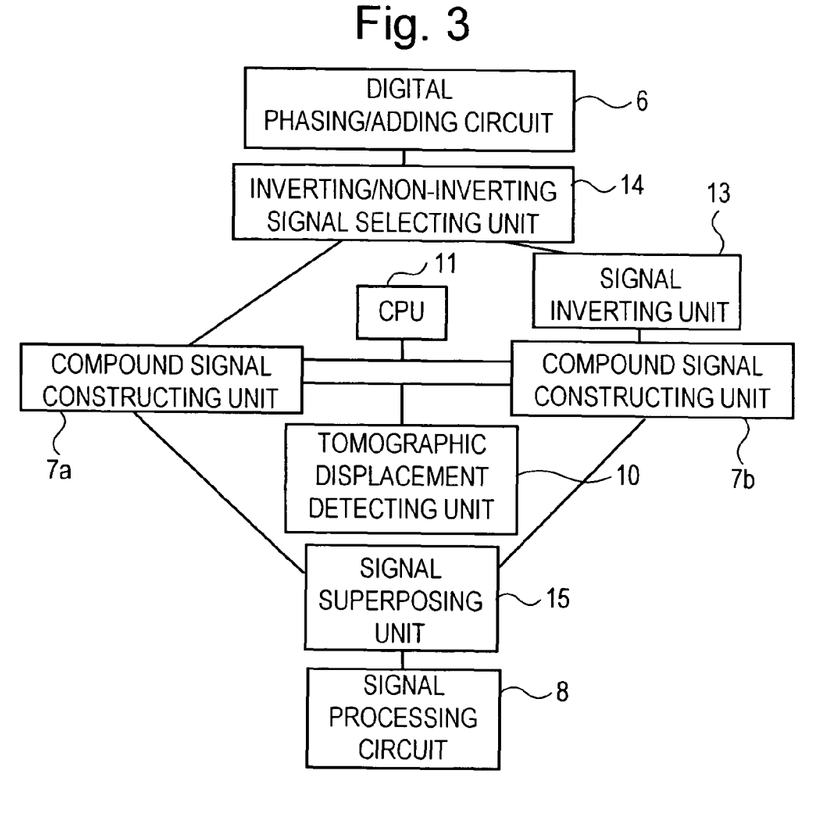
FIG. 3 is a block diagram showing still another embodiment of an ultrasonic imaging apparatus according to the present invention.

FIG. 3 is a block diagram showing an ultrasonic imaging apparatus according to a Third embodiment of the present invention for obtaining a second harmonic image. As shown in the figure, according to this embodiment, the apparatus in the First embodiment is further provided with two compound signal constructing units 7a and 7b; a signal inverting unit 13 for inverting the phase of a received beam signal output by the digital phasing/adding unit 13; an inverting/non-inverting signal selecting unit 14 for determining whether to send the received beam signal to the signal inverting unit 13 or to the compound signal constructing unit 7a as it is; and a signal superposing unit 15 for adding two compound signals which are respectively synthesized by the two-system compound signal constructing units 7a and 7b and for extracting higher harmonic signals.

Since the apparatus is constructed as described above, received beam signals output by the digital phasing/adding circuit 6 are transmitted to the inverting/non-inverting signal selecting unit 14, and received beam signals for the image first input are transmitted to the compound signal constructing unit 7a, without inverting the phase of the signals. Then, as in the case shown in FIG. 1, a compound signal is created and is transmitted to the signal superposing unit 15. Next, the received beam signals for the image input to the inverting/non-inverting signal selecting unit 14 are phase-inverted by the signal inverting unit 13, and they are then output to the signal superposing unit 15. In the signal superposing unit 15, compound signals output by the compound signal constructing units 7a and 7b are added up and output to the signal processing circuit 8. In this manner, when compound signals are output by the compound signal constructing unit 7a, a signal is promptly added by the signal superposing unit 15 to the immediately preceding signal output by the compound signal constructing unit 7b, and the result is output. When a new compound signal is output by the compound signal constructing unit 7b, this signal is added to the immediately preceding signal output by the compound signal constructing unit 7a. Thus, a second harmonic signal can be extracted and visualized without lowering the frame rate when compound signals are input to the compound signal constructing units 7a and 7b.

In the above description, the calculation is performed while inverting the phases of the received beam signals: however, the same effect is obtainable by inverting the phase of the transmitted waveform. Further, because the apparatus according to this embodiment also is characterized by acquisition of the above-mentioned compound signal image, a cross-sectional image having a high quality, which cannot be obtained by a mere higher harmonic cross-sectional image, is obtainable.

Fourth Embodiment

According to each of the above-described embodiments, it is possible to construct a compound image while enlarging and displaying the field angle of an ultrasonic cross-sectional image. Even when the field angle does not need to be enlarged, if a compound image can be displayed, not only is the user's option broadened, but also a compound image with high quality is provided.

Figure 4:
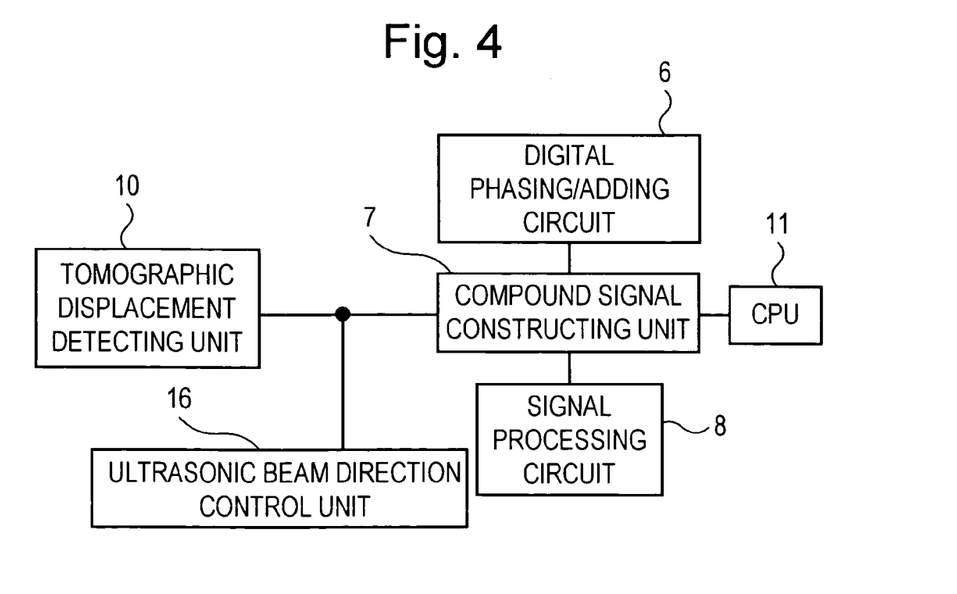
FIG. 4 is a block diagram showing still another embodiment of an ultrasonic imaging apparatus according to the present invention.

FIG. 4 is a block diagram showing an ultrasonic imaging apparatus according to a Fourth embodiment of the present invention. The apparatus according to this embodiment is similar to the First embodiment and is equipped with an ultrasonic beam direction control unit 16 for controlling the direction of transmitted and received ultrasonic beams in accordance with the amount of positional displacement between a cross-sectional image and an ultrasound probe.

Figure 7A:
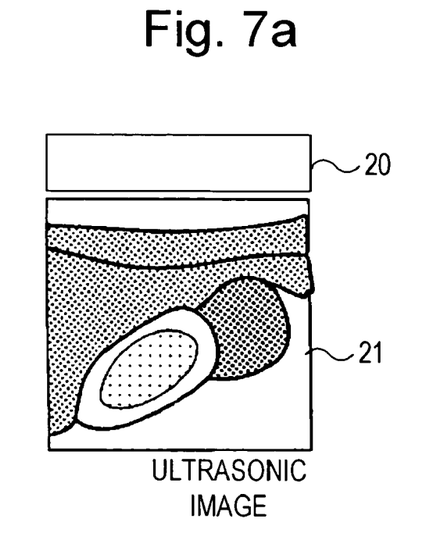
FIGS. 7a and 7b are diagrams showing one mode of the compound synthesis based on a oblique scan.
Figure 7B:
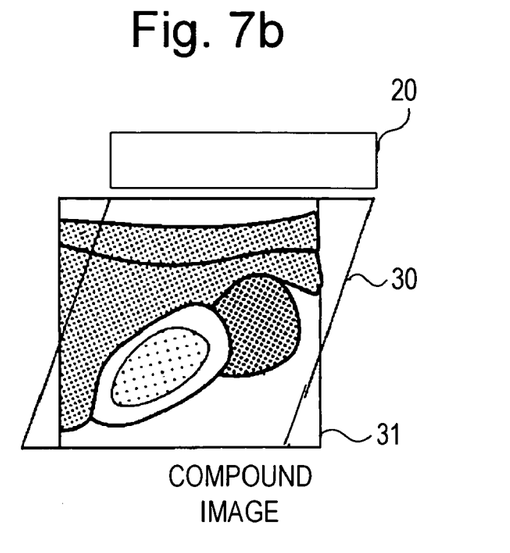
Figure 8:
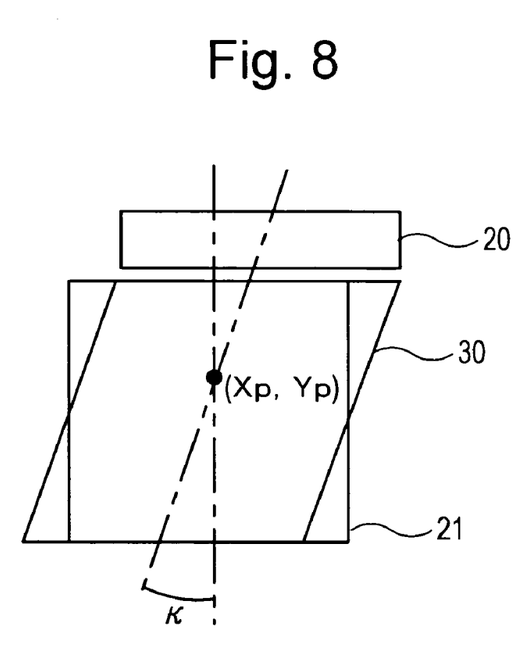
FIG. 8 is a diagram illustrating a method of compound synthesis based on a oblique scan.
Figure 9A:
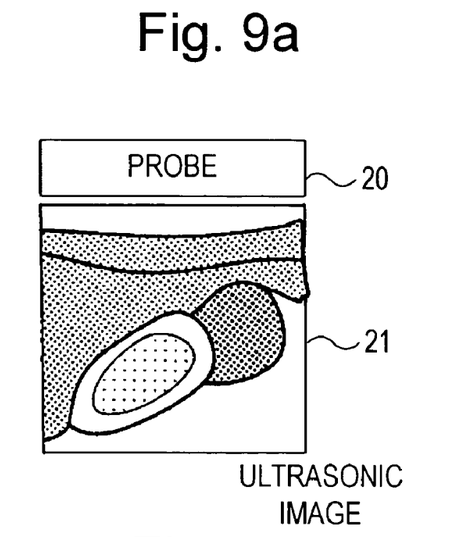
FIGS. 9a to 9d are diagrams showing another mode of the compound scan performed by a linear-type scanning probe.
Figure 9B:
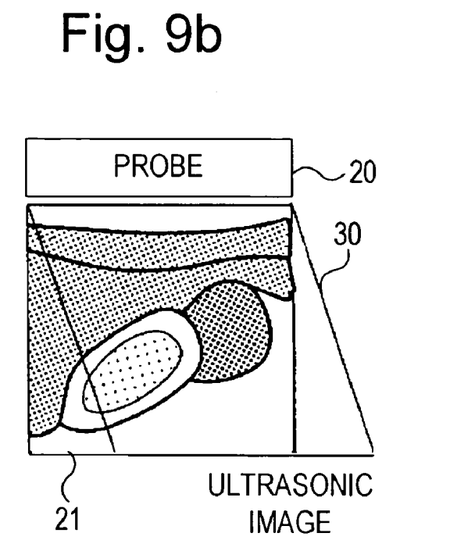
Figures 9C, 9D:
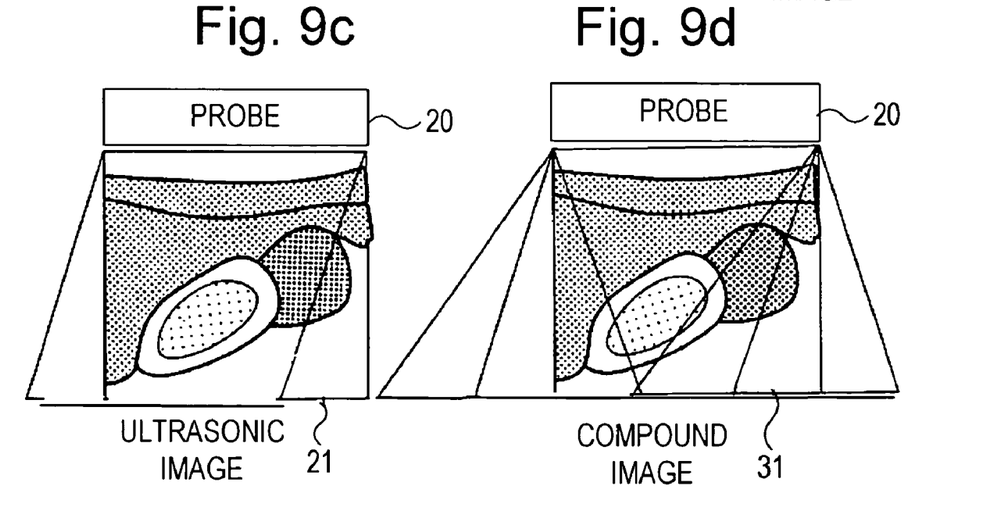

When the apparatus is thus constructed, by controlling the ultrasonic beams so that the beams are constantly superposed on an initial image which serves as the standard, a compound cross-sectional image with higher quality is obtainable. The displacement amount output by the cross-sectional image displacement detecting unit 10 is transmitted to the compound signal constructing unit 7 and to the ultrasonic beam direction control unit 16. In the compound signal constructing unit 7, a compound signal is created from the displacement amount and the received beam signals output by the digital phasing/adding circuit 6, as in the case of FIG. 1. Meanwhile, in the ultrasonic beam direction control unit 16, the beam direction is controlled so that beams are constantly directed to an area of the initial image. For example, if the position of the probe 20 for obtaining an initial image 21, as shown in FIG. 7(*a*), is moved laterally, as shown in FIG. 7(*b*), the direction of the ultrasonic beams is controlled so that the beams are constantly directed to the initial image area and an ultrasonic image 30 is acquired. In this case, as shown in FIG. 8, a beam passing position (Xp, Yp) for constructing a desired image in relation to a beam located on the center of the initial image 21 is set. Then, the beam direction is calculated by the following formula:

$$\kappa = \mathrm{atan}\{(X-Xp)/Yp\} - \theta$$

κ: a direction of the beams constructing the scanning plane desired in relation to the beam direction in an initial image Xp: a beam passage address in relation to the initial image (direction of received beam scanning)

Yp: a beam passage address in relation to the initial image (direction of the received beam)

Here, (Xp, Yp) may be input from a console by a user, or it may be automatically set to be the center of a displayed image. A formula utilizing the formula κ for finding the address of the received beam signal RAM, in which the original received beam signal is stored, from displacement information of a cross-sectional image and a memory address for creating a compound signal, as in the First embodiment, is set forth below, for example:

$$\{(Xc-X)(1+\sin\theta)(1-\sin\theta)+(Yc-Y)\cos\theta\sin\theta\}/\{(\alpha(1+\sin\theta)(1-\sin\theta)Yb=(Yc-Y)\cos\theta/\{\beta(1+\sin\theta)(1-\sin\theta)\}=Xb$$

X: a probe position on a coordinate axis horizontal to the initial image

Y: a probe position on a coordinate axis vertical to the initial image

θ: a beam direction in relation to the direction downward from the initial image Xb: an address of the received beam signal RAM (direction of received beam scanning)

Yb: an address of the received beam signal RAM (direction of the received beam)

Xc: an address of the compound signal RAM (horizontal direction of the display monitor)

Yc: an address of the compound signal RAM (vertical direction of the display monitor)

α: an amplification coefficient between the beam signal RAM and the sound speed map RAM (direction of received beam scanning)

β: an amplification coefficient between the beam signal RAM and the sound speed map RAM (direction of the received beam)

The example shown in FIG. 7 relates to a case where the probe is moved. However, as shown in FIG. 9(a) to 9(d), a compound synthesis can be conducted not only by moving a probe 20, but instead by controlling the direction of ultrasonic beams to cause them to be oblique, whereby the same effect as described for the above-described embodiment is obtainable.

Figure 10A:
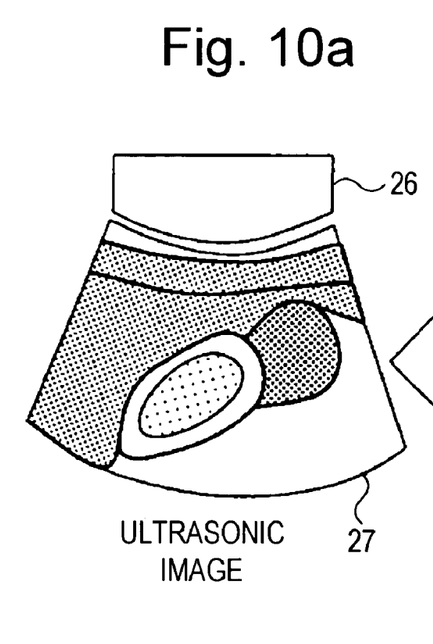
FIGS. 10a and 10b are diagrams showing another mode of the compound scan performed by a convex scanning probe.
Figure 10B:
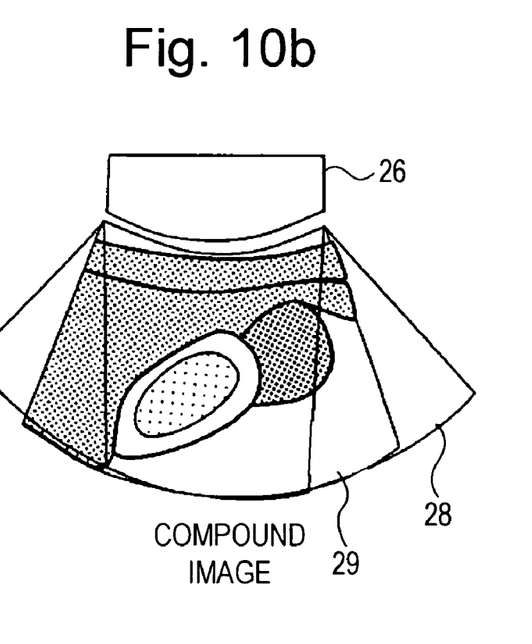

Further, in a scan using a convex probe on which transducers are arranged in an arcuate line, in addition to the above-mentioned method of performing an oblique scan, there is a method of moving the field angle, as shown in FIG. 10(a) and 10(b). In this case, the conversion performed in the compound signal synthesizing unit is simple, it is not necessary to prepare in advance focus data for the oblique scan, and focus data acquired from the front of an opening can be utilized. Of course, when a convex probe is used, oblique scanning and a shift of the field angle may be utilized in combination.

In the embodiment described above, a two-dimensional cross-sectional image is obtained by using a one-dimensional transducer array: however, the present invention is not limited thereto, but is also applicable when a two-dimensional image or a three-dimensional image is displayed by using a ring array or a two-dimensional transducer array.

Fifth Embodiment

Figure 11:
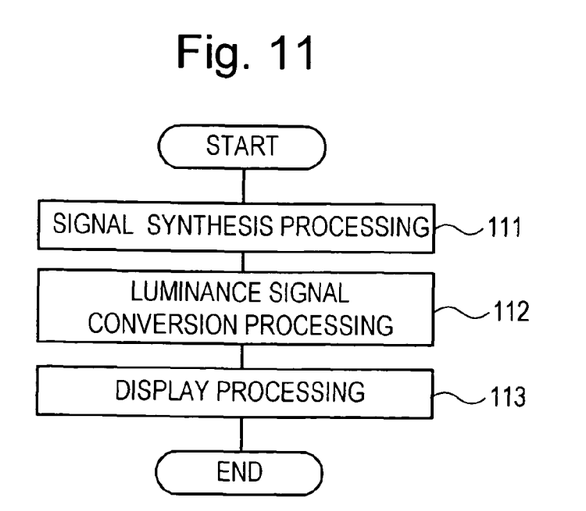
FIG. 11 is a flow chart illustrating the operation of the embodiments of an ultrasonic imaging apparatus according to the present invention as performed by software.

FIG. 11 is a flow chart showing the process in a case where an ultrasonic imaging apparatus is operated by software. The CPU 1 of the ultrasonic imaging apparatus in FIG. 1 uses the respective components in FIG. 1 and is operated according to the process shown in FIG. 11.

(Step 111. Signal Synthesizing Process)

First, an operator gives an initial instruction for setting the functions of the ultrasonic imaging apparatus. For example, before beginning examination, an instruction to obtain a compound image is given to the apparatus. In this case, the operator can select the functions of producing a compound image from ultrasonic beams or performing image synthesis using luminance signals, or performing compound image synthesis while enlarging the field angle or performing compound image synthesis without enlarging the field angle. For this purpose, an image synthesis mode switching device may be provided to a console so as to perform compound image synthesis in a selected mode.

After thus selecting the functions of the ultrasonic imaging apparatus, the operator applies a probe 4 to a portion of the object to be examined and inputs instructions to begin an ultrasonic scan from an operating device. In response thereto, selection of an aperture, transmission delay data, and reception delay data are set from the CPU 11 to a transducer selecting switch 3, a transmission circuit 1, and a reception circuit 5, respectively. Further, a compound signal constructing circuit 7 is selected in response to instructions to select a mode of compound image synthesis, and an ultrasonic beam scan is started. In the scan, driving pulses to which time delays are respectively applied are input from the transmission circuit 1 into the transducer selecting switch 3 via a transmission/reception separating circuit 2 corresponding to each of the transducers forming an aperture of the probe 4. Connection switching is carried out by the transducer selecting switch 3 so that the driving pulses are output to corresponding transducers. By this operation, the selected transducer group is driven by the driving pulses output by the transducer selecting switch 3.

In the selected transducer group, the transducers are driven in ascending order of time delay to transmit ultrasonic waves to the inside of a living body. The time delay of the ultrasonic waves transmitted to the inside of the living body is adjusted by the transmission circuit 1 so that the wave surfaces of the ultrasonic waves transmitted by the respective transducers arrive at a predetermined transmitted wave focal point with the same time phase. If there are tissues encountered that have different acoustic impedances in the path of propagation, a part of the ultrasonic waves will be reflected at its interface, and reflected waves (echo) return towards the probe. Echoes sequentially return towards the probe in accordance with the depth at which they are propagated. These echoes are received by the transducers that were driven in ultrasonic wave transmission or successive transducer groups whose aperture is switched to become large with the passage of time, and the waves are converted into electrical echo signals.

The echo signals which are converted into electrical signals by the transducers are input to the reception circuit 5 via the transducer selecting switch 3 and the transmission/reception separating circuit 2, and here, they are separately subject to amplification processing at each element line (channel) of the transducers, and are converted into digital signals in the respective channels. In a digital phasing/adding unit 6, digitalized echo signals which are separately given a time delay in correspondence with the respective transducers are delayed at each channel and are added up. That is, additions are made to the signals so as to cause them to have uniform time phases, as if echoes reflected at a certain point in the object (each point on received beams) appeared at the same time, and any noise included in the echoes is thus reduced. Further, filtering processing is performed so as to extract a signal in a necessary signal band and acquire a received beam signal. These processings at the reception circuit 5 are known as a dynamic focus method.

The received beam signal generated by the reception circuit 5 is input into a compound signal constructing unit 7 and is subject to compound synthesis processing according to the present invention. That is, it is a characteristic of the present invention that received beam signals having phase information, before conversion into luminance signals, are generated and are made to interfere with each other, thereby improving the S/N ratio. Accordingly, the compound signal constructing unit 7 is constructed so as to be able to utilize a complex signal and to operate at high speed, which is different from the conventional system. Here, the object of producing a compound image is, as described above, to clearly image the interface of mediums parallel to one ultrasonic beam in the object to be examined and to reduce dark portions generated behind a body producing multiple reflections or a strongly reflecting body by superposing images obtained from multiple directions. Therefore, another image of one cross-section is obtained with ultrasonic beams at a different position or in a different direction, and those two images are combined. Since, in this synthesis, received beam signals acquired from an identical portion of the object have to be combined, it is necessary to find the relation among the directions of the received beams, the received beam signals, and the depth, to find the positional relation between these beams and the object, and to make adjustments for the positional relation between the received beam signals of two images so as to combine them.

The compound signal constructing unit 7 according to this embodiment has two RAMs, including memory cells with addresses which are two-dimensionally arranged corresponding to a scanning plane of the ultrasonic beams. One is a received beam signal RAM for storing a received beam signal which is currently measured and input, and the other is a compound signal RAM for storing a received beam signal measured previously or a compound signal. The addresses of those RAMs are set corresponding to a two-dimensional scanning plane based on the transducer direction (vertical direction).

Here, the central position and the direction of the probe are detected by a cross-sectional image displacement detecting unit 10. This cross-sectional image displacement detecting unit 10 employs, for example, a known method of finding the position and direction of the ultrasound probe to the object from the mutual relation between a plurality of sequentially obtained images. It is thereby possible to avoid the difficulty of performing a scan on the object while detecting the position and the direction of the probe attached to a mechanical position detecting device. However, the present invention is not limited thereto, and a mechanical position detecting device also may be employed. Further, a known magnetic sensor also may be used.

On the basis of the thus-detected central position and direction of the probe, and of the estimated value of the speed of sound in the medium and the time between ultrasonic transmission and reception, the relation between a received beam signal and the depth is calculated from the path distance of the ultrasonic waves, and portions of received beam signals corresponding to that depth are stored in the memory cells of the received beam signal RAM with corresponding addresses.

Meanwhile, in the compound signal RAM, produced compound signals measured before the previous transmission (in the initial state, a received beam signal) are stored in the same manner as in the above-described received beam signal RAM. Therefore, by reading out signals from these two RAMs corresponding to the same portion of the object and performing a calculation, the received beam signal and the compound signal can be synthesized. However, it is necessary to establish a correspondence between the address of the compound signal RAM and the received beam signal RAM because the position and the direction of the probe are different in these two RAMs.

Next, the compound processing will be described in detail.

For example, on the basis of the compound signal RAM, the address of the memory cell of the received beam signal RAM which stores the received beam signal that should be stored superposed in the memory cell of the compound signal RAM is found. If the corresponding received beam signal is not stored in the memory cell at the above-calculated address, the address is accordingly calculated by interpolation using a known method. Then, the corresponding received beam signal is stored superposed in the memory cell of the compound signal RAM. By performing this processing over all the memory cells of the compound signal RAM, the received beam signals obtained in the two measurements can be combined. The compound signal of the compound signal RAM is output to a signal processing circuit 8. The signal processing circuit 8 performs detection, logarithmic compression, and y-correction on the compound signal so as to generate an image signal, i.e., a luminance signal, and this signal is displayed on a display monitor via a display unit 9.

As a formula for finding the address of the memory cell of the received beam signal RAM to synthesize the above-described compound signal, for example, the formula mentioned in connection with the First embodiment is used.

(Step 112. Processing of Converting the Image Signal Into a Luminance Signal)

In the above-described manner, ultrasonic wave transmission and reception and signal processing of the reflected signal are repeatedly performed while transducers are selected and switched or the direction of ultrasonic beams is changed, and an image is formed from the received beam signals input after each transmission. Stored contents formed into an image in the memory are read out in sync with the scan of a CRT display monitor or the like, and those images are sequentially processed by the compound signal constructing unit 7.

(Step 113. Display Processing)

The compound signals sequentially processed are displayed as a compound image. According to this embodiment, it is a characteristic of the invention that compound synthesis is performed using a complex signal before conversion of the image signal into a luminance signal and after it has been subjected to phasing and addition, as in the First embodiment. Consequently, because phase information of the received beam signals is not lost, the S/N ratio can be improved by combining the beams and thus making them interfere with each other.

Further, according to the Fifth embodiment, the First embodiment is operated by software. However, it is needless to say that the Second to Fourth embodiments also may be operated by software when those embodiments are modified as described in connection with the First embodiment.

Further, in the embodiments shown in FIG. 2 and FIG. 4, it is also possible to perform compound synthesis by using a received beam signal after conversion into a luminance signal, i.e., a received beam signal in which the phase information has disappeared.

Further, in a known ultrasonic imaging apparatus that is constructed to attenuate a high-luminance portion producing multiple reflections, signals in a portion originally having a multiple signal are attenuated in some cases, and, thereby, the sensitivity therein might be deteriorated. However, by utilizing these embodiments in combination, it is possible to effectively reduce the low-luminance portion to a point where it is insignificant.

Further, when an ultrasonic signal in the object passes through an interface between extremely different acoustic impedances, ultrasonic energy is scattered in a portion deeper than this interface and is thus attenuated (back scattering). By using, in combination, a known ultrasonic imaging apparatus constructed to correct such a phenomenon and this embodiment, the image quality can be further improved.

As described above, according to the present invention, the S/N ratio of a compound image can be improved.

What is claimed is:

1. An ultrasonic imaging apparatus comprising:
   means for adding phase components of a plurality of digital echo signals, received from an ultrasound probe to generate a plurality of received beam signals;
   position detecting means for generating a relative displacement signal indicative of a positional relationship between the probe and an object to be examined;
   compound signal constructing means for complex combining first and second received beam signals using the relative displacement signal to generate a compound beam signal;
   means for converting the compound beam signal into a luminance signal; and
   means for displaying the luminance signal.

2. An ultrasonic imaging apparatus according to claim 1, wherein the combining means includes means for acquiring a first received beam signal from the ultrasound probe when it has a first positional relation to the object and means for acquiring a second received beam signal from the ultrasound probe when it has a second positional relation to the object, which is different from the first positional relation, and the first received beam signal and the second received beam signal are combined to produce said compound beam signal.

3. An ultrasonic imaging apparatus according to claim 1, wherein the position detecting means finds positional relations to the object that are different from each other by means of a position detecting sensor.

4. An ultrasonic imaging apparatus according to claim 1, wherein the compound signal constructing means combines the second received beam signal and the first received beam signal by storing the second received beam signal in a memory while superposing it on a received beam signal corresponding to a scanning plane of the ultrasonic beams.

5. An ultrasonic imaging apparatus according to claim 1, wherein the compound signal constructing means performs field angle enlargement processing in generating the compound beam signal.

6. An ultrasonic imaging apparatus according to claim 1 further comprising sound speed distribution measuring means for finding a distribution of a sound speed in a medium on an ultrasonic scanning plane on the basis of cross correlation among echo signals of the respective transducers forming the received beam signals, wherein the compound signal constructing means corrects the positional relation between the received beam signals and the object in accordance with the sound speed distribution.

7. An ultrasonic imaging apparatus according to claim 1 comprising signal inverting means for inverting the polarity of a received beam signal, wherein the compound signal constructing means generates compound beam signals respectively from the received beam signal and from an inverted received beam signal output by the signal inverting means and adds up the thus generated synthesized received beam signals.

8. An ultrasonic imaging apparatus according to claim 1 further comprising transmitted wave focusing means for controlling a direction of the ultrasonic beam on the basis of a position and a direction of the ultrasound probe relative to the object, which are detected by the position detecting means.

9. An ultrasonic imaging apparatus according to claim 1 further comprising sound speed layer structure measuring means for measuring the sound speed layer structure of mediums on an ultrasonic scanning plane on the basis of cross correlation of echo signals of the respective transducers forming the received beam signals, wherein the compound signal constructing means corrects for distortion of path distance and time of the received beam signals on the basis of the sound speed layer structure.

10. An imaging data processing method for an ultrasonic imaging apparatus comprising the steps of:
    acquiring a first received beam signal from an ultrasound probe having a first positional relation relative to an object to be examined;
    acquiring a second received beam signal from the ultrasound probe having a second positional relation relative to the object, which is different from the first positional relation;
    matching a phase of the first received beam signal with a phase of the second received beam signal;
    complex combining the second received beam signal with the first received beam signal;
    converting the synthesized received beam into a luminance signal; and
    displaying the luminance signal.

11. An imaging data processing method for an ultrasonic imaging apparatus according to claim 10, wherein the combining step includes the step of adding up the second received beam signal subjected to the coordinate transformation and the first received beam signal.

12. An imaging data processing method for an ultrasonic imaging apparatus according to claim 11, wherein, in the adding step, luminance information and phase information of the second received beam signal which has been subjected to coordinate transformation and information of the first received beam signal are subjected to complex addition.

13. An imaging processing program in an ultrasonic imaging apparatus comprising the steps of:
    matching phases of a plurality of received beam signals from an ultrasound probe having various positional relations relative to an object to be examined;
    complex combining the plurality of received beam signals to produce synthesized received beam signals;
    converting the synthesized received beam signals into luminance signals; and
    displaying the luminance signals.

14. An imaging data processing program in an ultrasonic imaging apparatus comprising the steps of:
    acquiring a first received beam signal by an ultrasound probe having a first positional relation to an object to be examined;
    acquiring a second received beam signal by the ultrasound probe having a second positional relation to the object which is different from the first positional relation;
    matching a phase of the first received beam signal with a phase of the second received beam signal;
    complex combining the second received beam signal with the first received beam signal to produce synthesized received beam signals;
    converting the synthesized received beam signals into a luminance signal; and
    displaying the luminance signal.

15. An imaging data processing program in an ultrasonic imaging apparatus according to claim 14, wherein the combining step includes the step of adding the second received beam signal that has been subjected to coordinate transformation and the first received beam signal.

16. An imaging data processing program in an ultrasonic imaging apparatus according to claim 15, wherein, in the adding step, complex addition is performed on luminance information and phase information of the second received beam signal that has been subjected to the coordinate transformation and of the first received beam signal.

17. An imaging data processing program in an ultrasonic imaging apparatus according to claim 13, wherein the combining step includes: the step of acquiring a first received beam signal from the ultrasound probe having a first positional relation to the object; the step of acquiring a second received beam signal from the ultrasound probe having a second positional relation to the object, which is different from the first positional relation; the position detecting step of detecting the first positional relation and the second positional relation; and the compound signal constructing step of combining the first received beam and the second received beam on the basis of positional relations detected in the position detecting step.

18. An imaging data processing program in an ultrasonic imaging apparatus according to claim 17, wherein, in the position detecting step, positional relations among a plurality of images sequentially obtained by the ultrasound probe having positional relations different from each other are found from the relation between the images.

19. An imaging data processing program for an ultrasonic imaging apparatus according to claim 17, wherein in the position detecting step, different positional relations between the ultrasound probe and the object are determined by a position detecting sensor.

20. An imaging data processing method for an ultrasonic imaging apparatus according to claim 10, further comprising a step of:
performing coordinate transformation on the second received beam signal so as to convert the coordinates of the position of the second received beam signal into the coordinates of the position of the first received beam signal.

21. An imaging data processing method for an ultrasonic imaging apparatus according to claim 14, further comprising a step of:
performing coordinate transformation on the second received beam signal so as to convert the coordinates of the position of the second received beam signal into the coordinates of the position of the first received beam signal.

* * * * *